United States Patent
Anquetil

(10) Patent No.: US 11,715,391 B2
(45) Date of Patent: Aug. 1, 2023

(54) INJECTION CARTRIDGE DETECTION

(71) Applicant: Portal Instruments, Inc., Cambridge, MA (US)

(72) Inventor: Patrick Armand Anquetil, Brookline, MA (US)

(73) Assignee: Portal Instruments, Inc., Cambridge, MA (US)

(*) Notice: Subject to any disclaimer, the term of this patent is extended or adjusted under 35 U.S.C. 154(b) by 280 days.

(21) Appl. No.: 17/225,962

(22) Filed: Apr. 8, 2021

(65) Prior Publication Data

US 2021/0319718 A1   Oct. 14, 2021

Related U.S. Application Data

(60) Provisional application No. 63/006,843, filed on Apr. 8, 2020.

(51) Int. Cl.
| | | |
|---|---|---|
| *G09B 23/28* | (2006.01) | |
| *A61M 5/30* | (2006.01) | |
| *A61M 5/315* | (2006.01) | |
| *G09B 5/00* | (2006.01) | |

(52) U.S. Cl.
CPC ............ *G09B 23/285* (2013.01); *A61M 5/30* (2013.01); *A61M 5/31586* (2013.01); *A61M 2005/31588* (2013.01); *A61M 2205/332* (2013.01); *A61M 2205/3317* (2013.01); *A61M 2205/3327* (2013.01); *A61M 2205/52* (2013.01); *A61M 2205/8206* (2013.01); *G09B 5/00* (2013.01)

(58) Field of Classification Search
CPC .......... G09B 23/285; G09B 5/00; A61M 5/30; A61M 5/31586; A61M 2005/31588; A61M 2205/3317; A61M 2205/332; A61M 2205/3327; A61M 2205/52; A61M 2205/8206
USPC ........................................ 434/262
See application file for complete search history.

(56) References Cited

U.S. PATENT DOCUMENTS

| | | | | |
|---|---|---|---|---|
| 10,092,703 | B2* | 10/2018 | Mounce | A61M 5/3202 |
| 2013/0280687 | A1* | 10/2013 | Edwards | G09B 23/285 |
| | | | | 434/262 |
| 2015/0100024 | A1* | 4/2015 | Baker | A61M 5/20 |
| | | | | 434/262 |
| 2015/0235571 | A1* | 8/2015 | Alexandersson | A61M 5/31501 |
| | | | | 434/262 |
| 2015/0302778 | A1* | 10/2015 | Helmer | G09B 23/285 |
| | | | | 604/230 |
| 2015/0379899 | A1* | 12/2015 | Baker | G09B 23/285 |
| | | | | 434/262 |
| 2019/0143044 | A1* | 5/2019 | Paramanandam | A61M 5/145 |
| | | | | 604/187 |
| 2021/0170094 | A1* | 6/2021 | Diperna | A61M 5/142 |
| 2021/0170095 | A1* | 6/2021 | Diperna | A61M 5/14248 |
| 2022/0339391 | A1* | 10/2022 | Gillerman | A61M 16/202 |

FOREIGN PATENT DOCUMENTS

WO    2017174672 A1    10/2017

\* cited by examiner

*Primary Examiner* — Michael C Grant
(74) *Attorney, Agent, or Firm* — Occhiuti & Rohlicek LLP

(57) ABSTRACT

A needle-free injector conditionally detects a training cartridge based on the detected response to linear actuation of a plunger and enters a training mode instead of an injection mode.

21 Claims, 9 Drawing Sheets

INJECTION CARTRIDGE DETECTION

RELATED APPLICATIONS

This application claims the benefit of priority under 35 USC 119 from the Apr. 8, 2020 filing date of U.S. Provisional Application 63/006,843, the contents of which are incorporated herein by reference.

BACKGROUND

Powered injectors such as needle-free injectors may have different operating protocols than manual needles and syringes, and may require training for new users. There remains a need for detecting when a needle-free injector should be placed in a training mode rather than an injection mode.

SUMMARY

A needle-free injector conditionally detects a training cartridge based on the detected response to linear actuation of a plunger and enters a training mode instead of an injection mode.

An injector disclosed herein includes a chamber that receives a cartridge, a plunger positioned to engage the cartridge when the cartridge has been placed in the chamber, a drive system coupled to the plunger for applying a linear force to drive the plunger into the chamber, wherein the drive system includes a rotary motor and a controller that controls a drive current to the rotary motor, a sensor system including a rotary encoder providing a signal indicative of a rotary position of the rotary motor and a drive signal indicative of a drive current supplied to the rotary motor, and a controller coupled to the sensor system and to the drive system, the controller comprising a memory having computer-executable code stored therein that configures the controller to select, based on information received from the sensor system, between a training mode for training a user of the injector in proper operation of the injector and an injection mode for delivering a needle-free injection from the cartridge, the information including the signal from the rotary encoder used by the controller to determine a linear position of the plunger and the drive signal used by the controller to determine a linear force applied by the drive system to the plunger, wherein the controller evaluates the manner in which the linear position of the plunger changes in response to the drive signal.

The drive signal may be a control signal provided by the controller to a motor controller for the rotary motor.

In another aspect, an injector disclosed herein includes a chamber that receives a cartridge, a plunger positioned to engage the cartridge when the cartridge has been placed in the chamber, a drive system coupled to the plunger for applying a linear force to drive the plunger into the chamber, a sensor system configured to detect a position of a plunger and a linear force applied by the drive system to the plunger, a memory, and a controller coupled to the sensor system and to the drive system, the controller being configured by computer executable code stored in the memory to select between a training mode and an injection mode based on a change in the position of the plunger in response to the linear force.

The sensor system may include a position sensor that detects the position. The sensor system may include a force sensor that detects the linear force. The drive system may include a rotary motor. The position sensor may include a rotary encoder that senses a rotary position of the rotary motor. The force sensor may include a current sensor configured to detect a drive current applied to the rotary motor. The force sensor may estimate the force based on a drive current supplied to the drive system, e.g., by directly measuring the drive current. In another aspect, the force sensor may estimate the force based on a control signal sent from the controller to a motor controller for the motor. For example, where the injector includes a separate motor controller or drive circuit that receives control signals from the controller and creates corresponding drive current(s) to produce a suitable mechanical (e.g., rotary) response from the motor, the controller may effectively operate as a force sensor, and use the controller output as a proxy for force applied by the motor.

In one aspect, the controller may select the training mode when a response of the plunger the linear force indicates that the plunger has encountered a force that varies with position of the plunger in a manner that encodes cartridge information for the controller. In another aspect, the controller may select the training mode when a response of the plunger to the linear force indicates that the plunger has encountered a force that blocks further distal linear movement of the plunger. In another aspect, the controller may select the training mode when a response of the plunger to the linear force indicates that, at a particular location, the plunger has encountered a force that blocks further distal movement of the plunger. In another aspect, the controller may be configured to, after having selected the training mode, operate the plunger at a controlled rate to simulate displacement of injectate from the injection cartridge in a needle-free injection. The controller may also or instead be configured to detect the training mode when the controller detects a substantially incompressible response of the cartridge at a predetermined linear position.

In another aspect, an injector described herein includes a chamber, a plunger positioned to engage a cartridge received in the chamber, a drive system that applies a force to the plunger, a sensor system configured to detect a position of the plunger, and a controller configured to select an operating mode for the injector based on a response of the plunger to linear actuation by the drive system.

The controller may be configured to select the operating mode based on a change of position of the plunger. The controller may be configured to select the operating mode based on the change of position in response to the force applied by the plunger. The operating mode may include one or more of a training mode, an injection volume mode, and an injection rate mode.

In another aspect, there is disclosed herein a training cartridge for a needle-free injector, the training cartridge comprising a body with an exterior surface shaped and sized for insertion into a chamber of the needle-free injector and a feature that causes a force that that resists displacement of a plunger that is being moved distally along an axis of the training cartridge, wherein the force varies with position along the axis, wherein the force enables the injector to determine that the cartridge is a training cartridge.

DESCRIPTION

In the following document, references to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth.

Recitation of ranges of values herein are not intended to be limiting, referring instead individually to any and all values falling within the range, unless otherwise indicated, and each separate value within such a range is incorporated into the specification as if it were individually recited herein. The words "about," "approximately" or the like, when accompanying a numerical value or physical property, are to be construed as indicating a deviation as would be appreciated by one of ordinary skill in the art to operate satisfactorily for an intended purpose. Similarly, words of approximation such as "approximately" or "substantially" when used in reference to physical characteristics, should be understood to contemplate a range of deviations that would be appreciated by one of ordinary skill in the art to operate satisfactorily for a corresponding use, function, purpose, or the like. Ranges of values and/or numeric values are provided herein as examples only, and do not constitute a limitation on the scope of the described embodiments unless explicitly stated otherwise. The use of any and all examples, or exemplary language ("e.g.," "such as," or the like) provided herein, is intended merely to better illuminate the embodiments and does not pose a limitation on the scope of the embodiments. No language in the specification should be construed as indicating any unclaimed element as essential to the practice of the embodiments.

In the following description, it is understood that terms such as "first," "second," "top," "bottom," "up," "down," and the like, are words of convenience and are not to be construed as limiting terms.

1 Needle-Free Transdermal Injection Device

Figure 1:
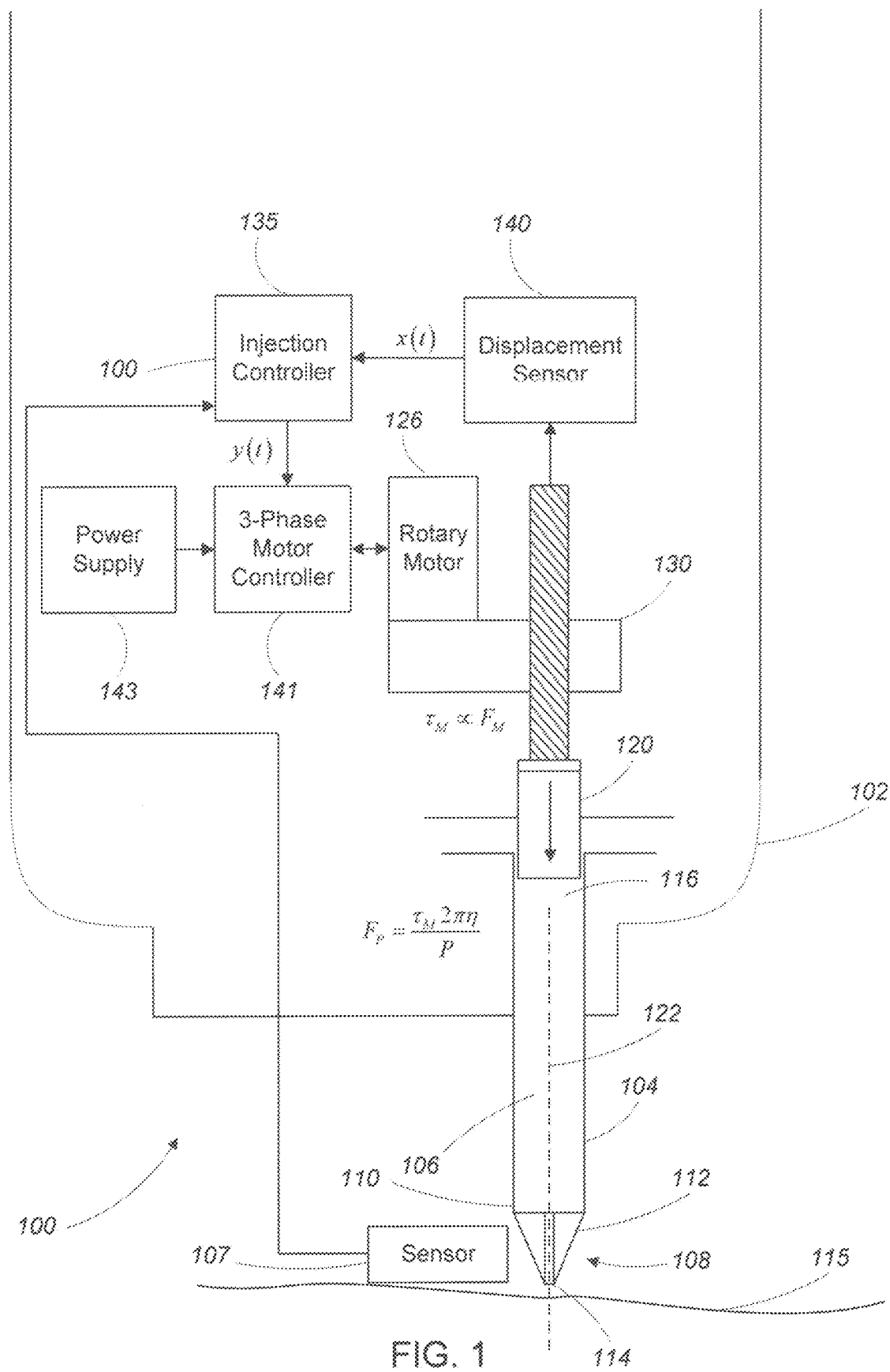
FIG. 1 is a schematic diagram of a controllable, needle-free transdermal injection device.

Referring to FIG. 1, a controllable, needle-free transdermal injection device 100 for transferring an injectate (e.g., a drug or a vaccine in any one of a number of states such as a liquid state or a powder state) through the skin of a patient includes a needle-free transdermal injector head 104 extending from a housing 102. The injector head 104 includes a chamber 106 for holding the injectate and a nozzle 108 disposed at a distal end 110 of the injector head 104. The nozzle 108 includes a head 112 and an opening 114 from which a jet of the injectate is discharged from the chamber 106. In operation, the opening 114 is placed near or against the skin 115 when the injectate is discharged.

The dimensions of the nozzle 108 may be adapted to control a shape and pressure profile of a stream of injectate exiting the nozzle 108. For example, the inner diameter of the opening 114 may be in a range of 50 micrometers to 300 micrometers and may employ a taper along the longitudinal axis 122 toward the opening to shape an exiting stream of injectate. It will also be appreciated that the geometry of the chamber 106 relative to the opening 114 may affect how linear motion of a plunger or the like within the chamber 106 translates into an exit velocity or pressure by an injectate through the opening 114. An outer diameter of the head 112 of the nozzle 108 may narrow to the opening 114 or may remain uniform or may expand to provide a suitable resting surface for the head 112 of the nozzle 108. The nozzle 108 may have a length along the longitudinal axis 122 of about 500 micrometers to about 5 millimeters. Similarly, the chamber 106 may have any suitable length along the longitudinal axis for containing an injectate, and for displacing the injectate through the opening 114 in one or more needle-free injections.

The chamber 106 may have a proximal end 116 and a distal end 110. An actuator (i.e., a piston or plunger 120) may be slidably disposed within the chamber 106. Movement of the plunger 120 along a longitudinal axis 122 in either direction can affect the pressure within chamber 106. In some embodiments, the chamber 106 is integral to the device 100. In other embodiments, the chamber 106 is separately attachable to device 100.

In some examples, the injection device 100 includes a sensor 107 (e.g., a mechanical sensor or a capacitive sensor) for detecting a contact between the apparatus and the skin of a patient. In some examples, the sensor 107 is configured to detect an angle of the cartridge relative to the skin of the patient. In some examples, the sensor 107 is configured to detect a position of the injection opening relative to the patient's skin 115 or body. In some examples, the sensor 107 communicates with the injection controller 100 to prevent injection from occurring when the apparatus is not in contact with the patient's skin 115 or when an angle or position of the apparatus relative to the patient is incorrect.

1.1 Rotary Motor

The injection device 100 may include an electromagnetic rotary motor 126 that applies a force to the plunger 120 via a linkage 130 to inject the injectate in the chamber 106 through the skin 115. The linkage may include a ball screw actuator 130, and the linkage may also or instead include any other suitable mechanical coupling for transferring a rotary force of the rotary motor 126 into a linear force suitable for displacing injectate from the chamber 106. For example, the linkage may include one or more of lead screws, linear motion bearings, and worm drives, or another other suitable mechanical components or combination of mechanical components. As noted above, linear motion may usefully be inferred from rotation of a lead screw, a rotary encoder, or the like, and the injection device 100 may be instrumented to monitor rotation in order to provide feedback on a position of the plunger 120 to a controller during an injection.

Figure 2:
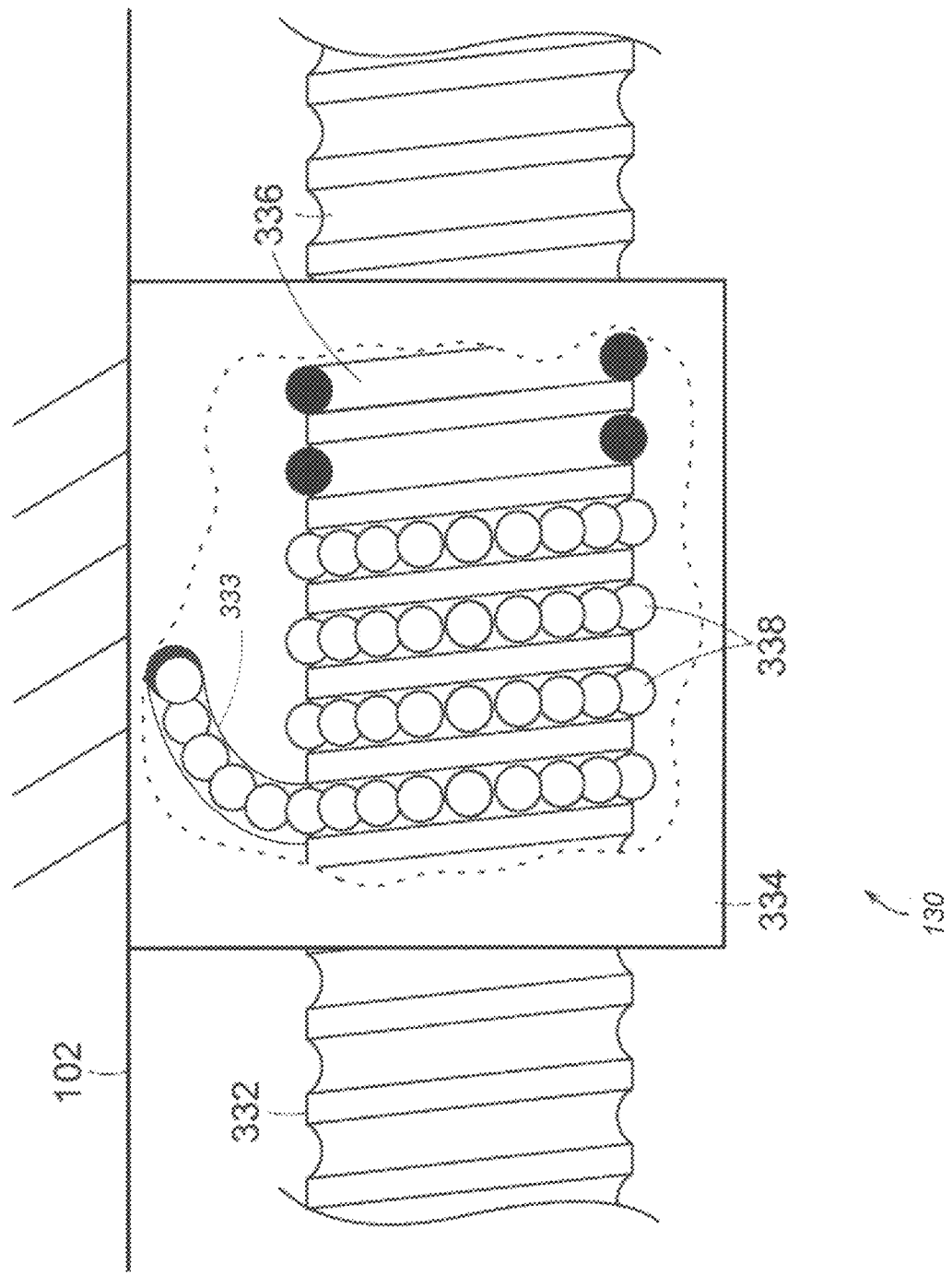
FIG. 2 is a cut-away diagram of a ball screw actuator.

Referring to FIG. 2, one example of a ball screw actuator 130 includes a screw 332 and a nut 334 (which is coupled to the housing 102 in FIG. 1), each with matching helical grooves 336. The ball screw actuator 130 may include a recirculating ball screw with a number of miniature balls 338 or similar bearings or the like that recirculate through the grooves 336 and provide rolling contact between the nut 334 and the screw 332. The nut 334 may include a return system 333 and a deflector (not shown) which, when the screw 332 or nut 334 rotates, deflects the miniature balls 338 into the return system. The balls 338 travel through the return system to the opposite end of the nut 334 in a continuous path. The balls 338 then exit from the ball return system into the grooves 336. In this way, the balls 338 continuously recirculate in a closed circuit as the screw 332 moves relative to the nut 334.

In some examples, the rotary motor 126 is of a type selected from a variety of rotational electrical motors (e.g., a brushless DC motor). The rotary motor 126 is configured to move the screw 332 of the ball screw actuator 130 back and forth along the longitudinal axis 122 by applying a torque (i.e., $\tau_M$) to either the screw 332 or the nut 334 of the ball screw actuator. The torque causes rotation of either the screw 332 or the nut 334, which in turn causes an input force $F_M(t)$, which is proportional to the torque applied by the motor, to be applied to the screw 332.

The torque $\tau_M$ applied to the screw 332 causes application of a force $F_P$ to the plunger 120 which in turn causes movement of the plunger 120 along the longitudinal axis 122. The force $F_P$ is determined according to the following equation representing an idealized relationship between torque and force for a ball screw actuator:

$$F_P = \frac{T_M 2\pi\eta}{P}$$

where $F_P$ is a force applied to the plunger 120 by the screw 332, $\tau_M$ is a torque applied to the screw 332, $\eta$ is an efficiency of the ball screw actuator 130, and P is a lead of the screw 332.

1.2 Control Loop

Referring again to FIG. 1, the transdermal injection device 100 may include a displacement sensor 140, an injection controller 135, and a three-phase motor controller 141. In general, the displacement sensor 140 measures a displacement x(t) of the screw 332 of the ball screw actuator 130 and/or the plunger 120. The displacement sensor 140 may, for example, measure an incremental displacement of the screw 332 by storing an initial displacement value (i.e., x(0)) and monitoring a deviation from the starting value over time. In other examples, the displacement sensor 140 measures an absolute displacement of the screw 332 relative to a position of the displacement sensor 140 or some other fixed reference point. In another aspect, the displacement sensor 140 may be coupled to a nut or other component of a ball screw that controls linear movement. In this configuration, the displacement sensor 140 can measure rotation of the screw drive, and rotational motion may be computationally converted into linear displacement for purposes of controlling operation of the device 100.

The displacement x(t) measured by (or calculated using data from) the displacement sensor 140 may be provided as input to the injection controller 135. As is described in greater detail below, the injection controller 135 processes the displacement x(t) to determine a motor control signal y(t). The motor control signal y(t) is provided to the three-phase motor controller 141 which, in conjunction with a power supply 143, drives the rotary motor 126 according to the motor control signal y(t). The motor 126 causes the torque $\tau_M(t)$ to be applied to the screw 332. The motor torque, $\tau_M(t)$ causes movement of the screw 332 (or any other suitable linear actuator) in a direction along the longitudinal axis 122.

1.3 System Diagram

Figure 3:
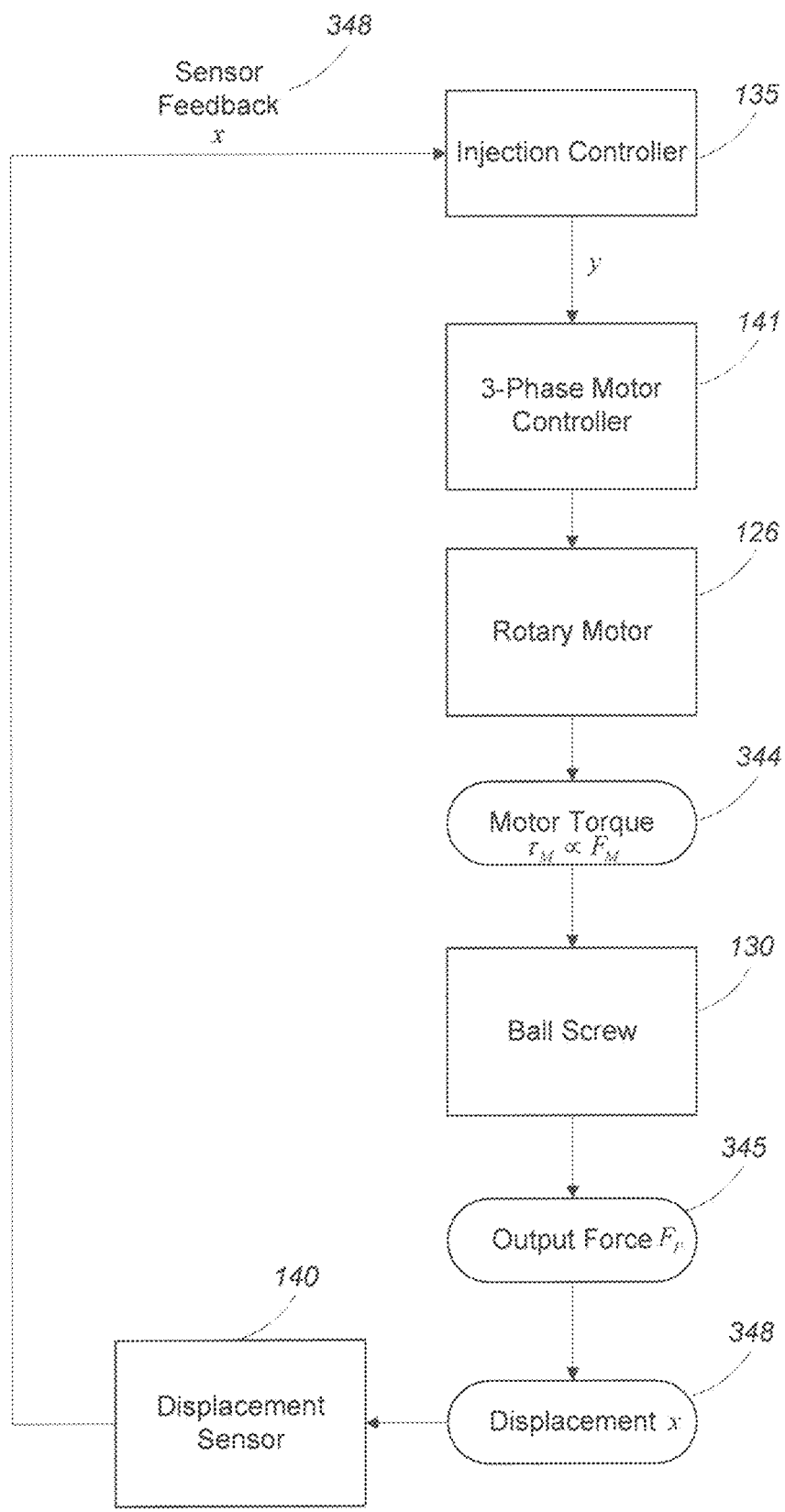
FIG. 3 is a block diagram of the controllable, needle-free transdermal injection device of FIG. 1.

Referring to FIG. 3, a schematic diagram of the system of FIG. 1 shows the rotary motor torque $\tau_M$ being applied to the ball screw 130 in step 344. Application of the rotary motor torque, at a given time $t_1$ by the rotary motor causes application of a force, $F_M(t_1)$ to the screw 332 of the ball screw 130 as shown in step 345, which in turn causes a displacement of the screw 332 in step 348.

The displacement of the screw 332 of the ball screw 130 is measured by the displacement sensor 140 and is fed back to the injection controller 135. As is described in greater detail below, the injection controller 135 processes the measured displacement to provide sensor feedback 348 to determine a motor control signal $y(t_1)$ which is supplied to the three-phase motor controller 141. The three-phase motor controller 141 drives the rotary motor 126 according to the motor control signal $y(t_1)$, causing the motor 126 to apply a torque $\tau_M(t_2)$ to the screw 332 of the ball screw 130 at a time $t_2$. As is noted above, the torque $\tau_M$ applied to the screw 332 causes application of a force $F_P$ to the plunger 120 with $F_P$ being determined as:

$$F_P = \frac{T_M 2\pi\eta}{P}$$

where $F_P$ is a force applied to the plunger 120 by the screw 332, $\tau_M$ is a torque applied to the screw 332, $\eta$ is an efficiency of the ball screw actuator 130, and P is a lead of the screw 332.

Figure 4:
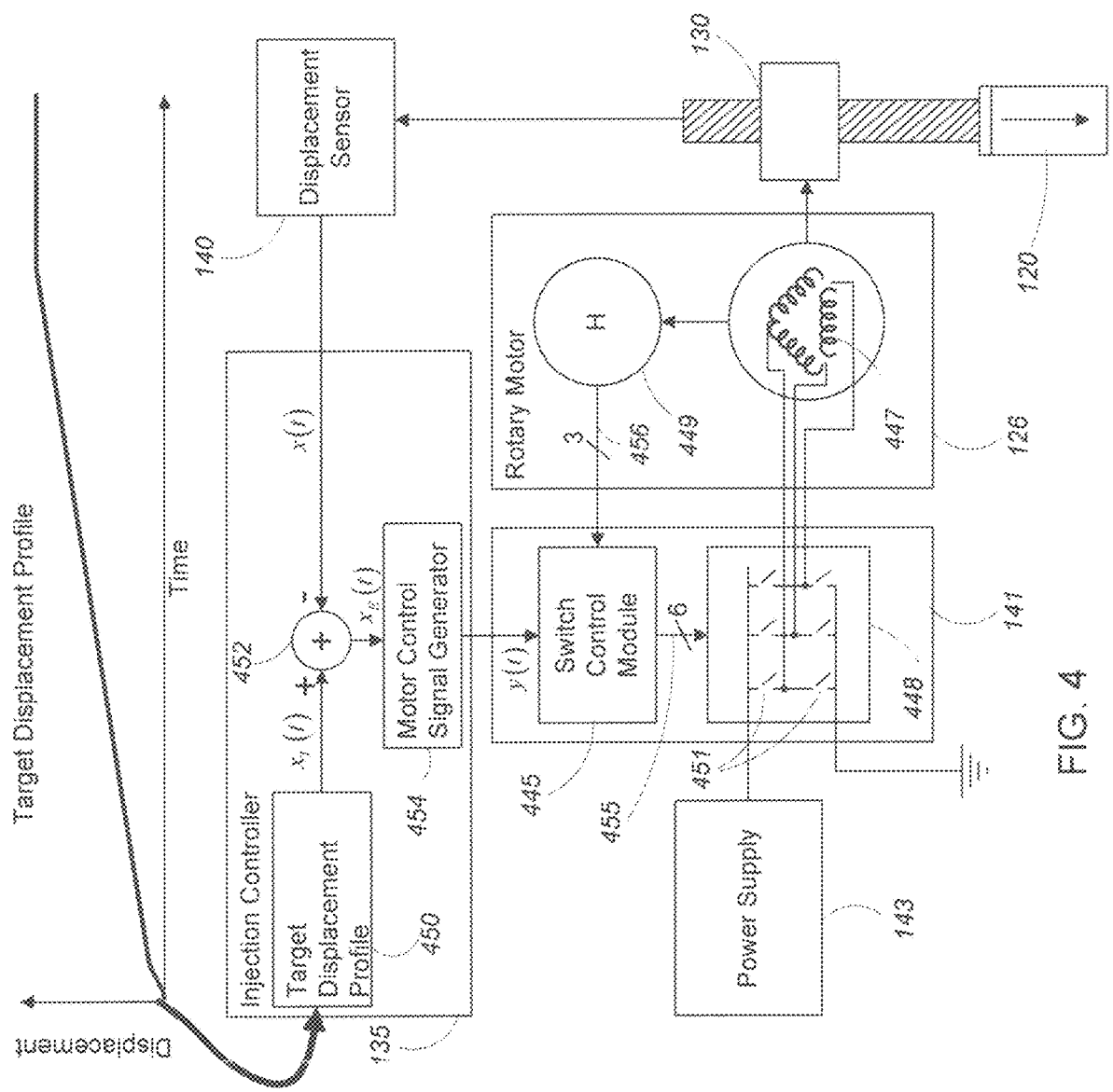
FIG. 4 is a detailed block diagram of the controllable, needle-free transdermal injection device of FIG. 1.

Referring to FIG. 4, in some examples the injection controller 135 includes a target displacement profile 450, a summing block 452, and a motor control signal generator 454. Very generally, the injection controller 135 receives a displacement value x(t) at time t from the displacement sensor 140. The time t is provided to the target displacement profile 450, which determines a target displacement value $x_T(t)$ for the time t.

In some examples, the target displacement profile 450 includes a mapping between target displacement values and times associated with an injection cycle (i.e., a range of time over which the plunger 120 of the device moves). For example, in the target displacement profile 450 shown in FIG. 4 the displacement starts at zero at the beginning of an injection cycle (i.e., at time $t_0$) and changes (e.g., increases) over time as the injection cycle proceeds, with each instant in time of the injection cycle being associated with a corresponding displacement value. As is described in greater detail below, in some examples the rate of change of the displacement values varies over time, with different time intervals of the injection cycle being associated with different rates of change of displacement values. Control of the plunger displacement, e.g., according to the target displacement profile 450, can be used to perform complex injections. For example, in one aspect, the plunger 120 is displaced relatively quickly during an initial piercing phase to penetrate the skin barrier, and in other time intervals the plunger 120 is displaced relatively slowly to deliver the injectate through an opening formed during the initial, piercing phase. In another aspect, the target displacement profile 450 may control multiple, sequential injections each having a biphasic profile with a piercing phase and a drug delivery phase. In practice, the actual displacement profile of the plunger 120 may vary from the ideal target displacement profile according to physical limits of the system and other constraints.

Both the measured displacement value x(t) and the target displacement value $x_T(t)$ are provided to the summing block 452. The summing block 452 subtracts the measured displacement value x(t) from the target displacement value $x_T(t)$ to obtain an error signal $x_E(t)$. The error signal $x_E(t)$ is provided to the motor control signal generator 454 which converts the error signal to a motor control signal y(t). The motor control signal y(t) is provided to the three-phase motor controller 141 or other suitable drive system, which in turn drives the motor 126 according to the motor control signal y(t).

In some examples, the rotary motor 126 may be a three-phase motor with three windings 447 and three Hall sensors 449, each Hall sensor 449 corresponding to a different one of the three windings 447. Each of the windings 447 is wrapped around a laminated soft iron magnetic core (not shown) so as to form magnetic poles when energized with current. Each of the three Hall sensors 449 generates a corresponding output signal 456 in response to presence (or lack of) a magnetic field in its corresponding winding 447.

The three-phase motor controller 141 includes a switch control module 445 and a switching module 448. The switching module 448 includes three pairs of switches 451 (with six switches 451 in total), each pair of switches corresponding to a different one of the windings 447 of the rotary motor 126 and configurable to place the corresponding winding 447 into electrical connection with the power supply 143 (whereby the winding is energized) or with ground. The switch control module 445 receives the motor control signal y(t) from the injection controller 135 and the three Hall sensor output signals 456 as inputs and processes the inputs to generate six switch control signals 455, each switch control signal 455 configured to either open or close a corresponding switch 451 of the switching module 448.

The above-described configuration implements a feedback control approach to ensure that a combination of the controlled torque applied to the screw 332 of the ball screw 130 due to the motor 126 causes the displacement of the plunger to track the target displacement profile 450 as the screw 332 is displaced.

1.4 Power Supply

Figure 5:
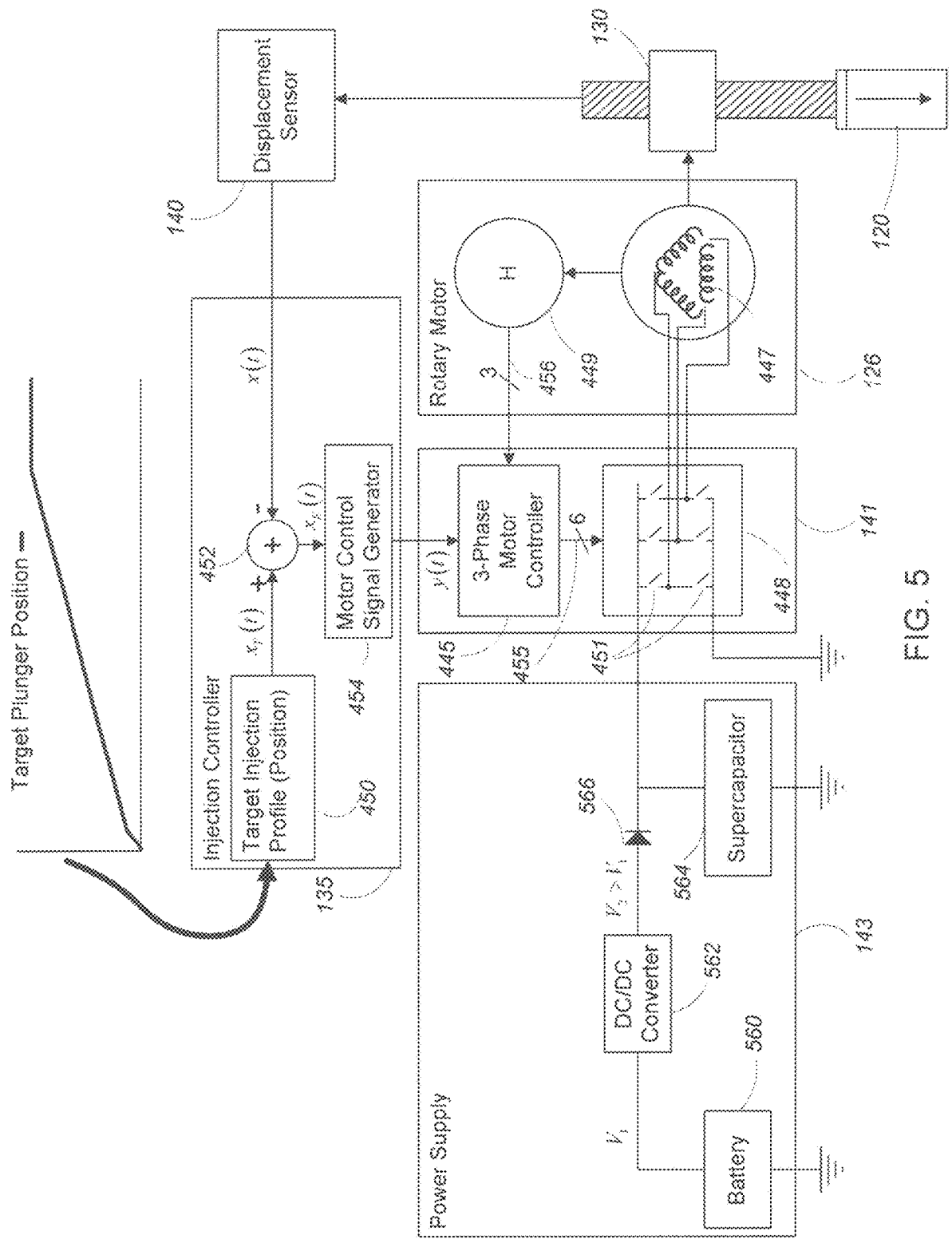
FIG. 5 is a detailed block diagram of the power supply of the controllable, needle-free transdermal injection device of FIG. 1.

Referring to FIG. 5, in some examples, the power supply includes a battery 560 (e.g., a Nickel Cadmium battery, a Nickel-Metal Hydride battery, a Lithium-ion battery, an alkaline battery, or any other suitable battery type) configured to supply a voltage $V_1$ to a DC/DC converter 562 (e.g., a boost converter). The DC/DC converter 562 receives the supply voltage $V_1$ from the battery 560 as input and generates an output voltage $V_2$ greater than $V_1$. In some examples, the DC/DC converter 562 is configured to boost the supply voltage by a factor in the range of 5 to 20. While the battery 560 may be rechargeable, the battery 560 may also usefully store sufficient energy for multiple injections, such as two or more one milliliter injections, e.g., from replaceable single-dose cartridges or from a single, multi-dose cartridge.

The output voltage $V_2$ may be provided in parallel to a supercapacitor 564 and to the switching module 448 of the three-phase motor controller 141 via a diode 566. In operation, the output voltage $V_2$ charges the supercapacitor 564 while the transdermal injection device 100 is inactive. When an injection operation commences, the switches 451 of the switching module 448 close (according to the switch control signals 455), connecting the windings 447 of the rotary motor 126 to the supercapacitor 564. This results in a discharge of the supercapacitor 564, causing current to flow through the windings 447 of the rotary motor 126 and induce rotation of the rotary motor 126.

In some examples, the supercapacitor 564 includes a number of supercapacitors coupled together with a switching network. When the transdermal injection device 100 is inactive, the switching network may be configured so that the number of supercapacitors is connected in parallel for charging. When an injection is initiated, the switching network may be reconfigured so that the number of supercapacitors is serially connected for discharge. In some examples, the supercapacitor 564 is configured to deliver a peak power of 200 Watts or more to the ball screw 130 via the rotary motor 126.

In general, the supercapacitor may be any high-capacity capacitor suitable for accepting and delivering charge more quickly than a battery or other source of electrical energy. A wide variety of supercapacitor designs are known in the art and may be adapted for use as the supercapacitor 564 contemplated herein, such as double-layer capacitors, pseudo capacitors, and hybrid capacitors. Similarly, the supercapacitor 564 may usefully include any number and arrangement of supercapacitors suitable for delivering electrical power in an amount and at a rate suitable for driving a rotary motor 126 of an injection device 100 as contemplated herein.

2 Target Displacement Profile

Figure 6:
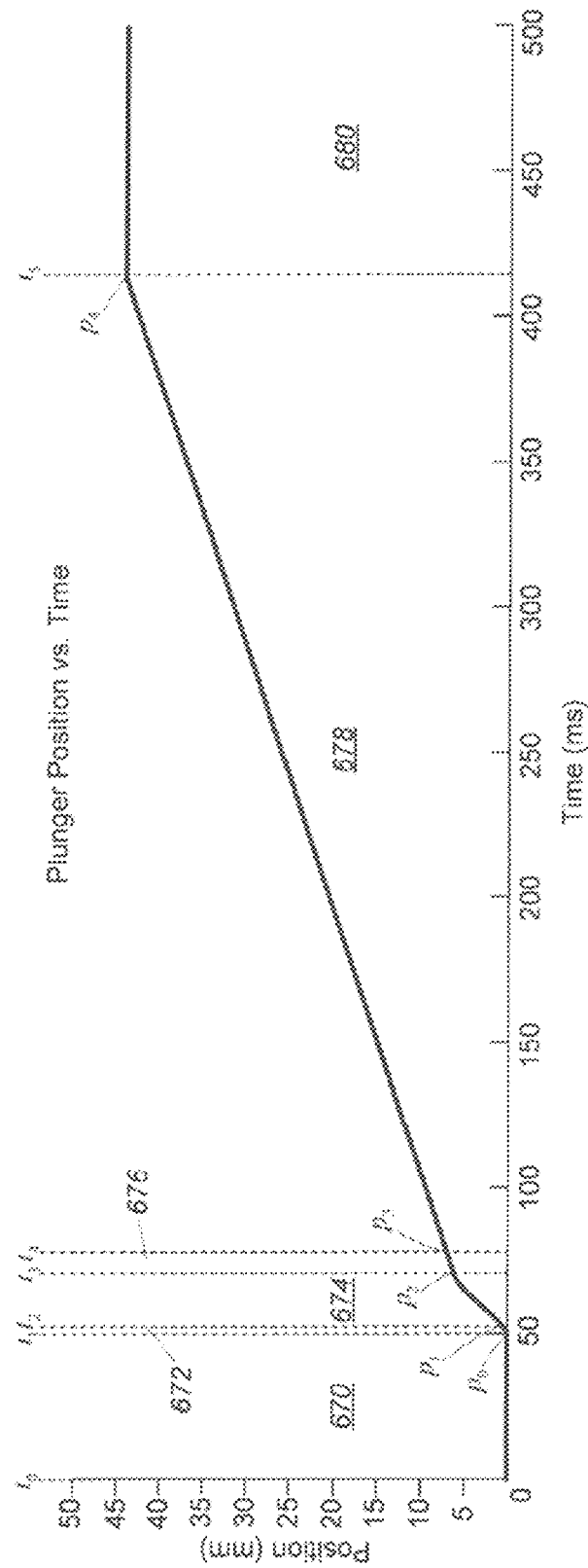
FIG. 6 is a target displacement profile.

Referring to FIG. 6, one example of a target displacement profile includes a number of injection phases, each associated with a corresponding time interval.

A first injection phase 670 is associated with a first time-interval extending from time $t_0$ to time $t_1$. In the first injection phase 670, the target displacement of the plunger 120 is at a constant initial position $p_0$ where the plunger 120 is engaged with the injectate in the chamber 106. In this phase, the injection device 100 is generally prepared to perform an injection operation. In general, the first injection phase 670 may be preceded by any number of preparatory steps or phases, such as loading of an injectate (or a cartridge containing an injected) into the injection device, the removal of bubbles from the injectate as necessary or appropriate, measuring environmental conditions, measuring parameters of an injection site, and any other steps or combination of steps useful for performing, or preparing to perform, a needle-free injection as contemplated herein.

In one aspect, the rotary motor 126 may be mechanically engaged with the ball screw actuator 130 (or any other suitable linear actuator) while the rotary motor 126 is stationary in the first injection phase 670. That is, the rotary motor 126 may be pre-engaged with the ball screw actuator 130 and preload to remove any mechanical slack in the mechanical components of the system. In this configuration, a mechanical switch or the like may be used to prevent relative movement of the components, and/or a gate or seal may be used at the nozzle exit to prevent leakage of drug from the chamber 106. In another aspect, the rotary motor 126 may be slightly spaced apart from engagement with the ball screw actuator 130. In this latter configuration, the rotary motor 126 may usefully accelerate (while unloaded) into engagement with the ball screw actuator 130 at an end of the first injection phase 670 or at a beginning of the second injection phase 672 to facilitate a greater initial velocity of injectate from the nozzle. This may, for example, include a single rotation of the rotary motor 126 from engagement with the ball screw actuator 130, or a fractional rotation suitable to facilitate very high initial rotational acceleration.

A second injection phase 672 is associated with a second time-interval extending from time $t_1$ to $t_2$. In the second injection phase 672, movement of the plunger 120 may be initiated. In this phase, the target displacement of the plunger 120 increases at a relatively high first rate to move the plunger 120 from the initial position $p_0$ to a first position $p_1$. In general, the motion of the plunger 120 in this phase may cause a jet of injectate to be ejected from the chamber 106 of the injector head 104 (via the opening 114) with a first velocity $V_1$ at least sufficient to pierce human tissue to a subcutaneous depth. In some examples, the second injection phase 672 spans a time interval less than 100 milliseconds (i.e., the difference between $t_1$ and $t_2$ is less than 100 milliseconds). In some examples, the second injection phase 672 spans a time interval less than 60 milliseconds (i.e., the difference between $t_1$ and $t_2$ is less than 60 milliseconds). In some examples, the second injection phase 672 spans a time interval less than 10 milliseconds (i.e., the difference between $t_1$ and $t_2$ is less than 10 milliseconds).

More generally, the injection device 100 may be configured so that in this second injection phase 672, the plunger 670 transitions from a stationary position to the target velocity at a sufficient rate for the initial stream of injectate to achieve a piercing velocity substantially instantaneously, e.g., without substantial leakage or loss of injectate at the surface. By configuring the linear drive system described above to accelerate in this manner from a fixed position to a piercing velocity, the injection device 100 may advantageously mitigate loss of injectate. As a further advantage, an injection device with this capability can usefully perform multiple sequential injections without requiring any physical recharge or resetting of a mechanical stored energy system.

A third injection phase 674 is associated with a third time-interval extending from time $t_2$ to $t_3$. In the third injection phase 674 the target displacement of the plunger increases at a rate substantially the same as the first rate to move the plunger 120 from the first position $p_1$ to the second position $p_2$. In this third injection phase 674, the plunger 120 may be moved at a rate to cause the jet of injectate to be ejected from the chamber 106 of the injector head 104 with a second velocity $V_2$ greater than or equal to the first velocity $V_1$. While the rate of plunger 120 movement and the velocity of the injectate stream may vary within this third injection phase 674, e.g., according to limitations on control precision, physical system components, and so forth, the plunger 120 should generally be driven at a minimum velocity suitable for piercing tissue at a target site to a desired depth for delivery of the injectate. The jet of injectate may also have a maximum velocity selected to avoid over-penetration or other undesirable tissue damage.

A fourth injection phase 676 is associated with a fourth time-interval extending from time $t_3$ to time $t_4$. In the fourth injection phase 676 the target displacement of the plunger 120 increases at a third rate, relatively slower than the first rate, to move the plunger 120 from the third position $p_3$ to a fourth position $p_4$. In this fourth injection 676, the injection device 100 may generally decelerate the plunger 120 to cause the jet of injectate to eject from the chamber 106 of the injector head 104 with a third velocity $V_3$ less than the first velocity $V_1$, which may generally be any velocity suitable for non-piercing delivery of additional injectate at a current depth of the stream of injectate within the target tissue.

A fifth injection phase 678 is associated with a fifth time-interval extending from time $t_4$ to $t_5$. In the fifth injection phase 678 the target displacement of the plunger 120 continues to increase at the third rate to move the plunger 120 from the fourth position $p_4$ to the fifth position $p_5$. In the fifth injection phase 678, the injection device 100 may generally deliver the injectate—typically a majority of the injectate in the chamber 106—at a subcutaneous depth achieved during the prior, piercing phase. The rate of movement may be generally constant or may otherwise vary consistent with maintaining subcutaneous drug delivery without further piercing of the tissue.

It will be appreciated that some continued piercing may occur during the fifth injection phase 678. Provided that any additional piercing does not create a pathway below subcutaneous depth within the target tissue that might result in loss or mis-delivery of therapeutic dosage, then this additional piercing will not affect the efficacy of transdermal drug delivery. It will also be understood that the total displacement of the plunger 120 will control the volume of drug delivered over the course of an injection, and a duration of the fifth injection phase 678 may correspondingly be selected according to an intended dosage.

Finally, a sixth injection phase occurs after time $t_5$. In the sixth injection phase the target displacement of the plunger 120 stops increasing, substantially halting the plunger 120 at a sixth position $p_6$. The sixth injection phase is associated with completion of the injection operation. As noted above, from this position, additional injection cycles may be initiated, provided of course that sufficient additional drug remains in the injection device 100 for completing additional injections.

In order to quickly achieve a piercing velocity and avoid loss of drug at the surface of an injection site, the second injection phase 672 (where acceleration of the injectate occurs) may be short relative to the piercing phase that is maintained once the piercing velocity is achieved. Thus, in some examples, the time interval associated with the third injection phase 674 is in a range of two to twenty times as long as the time interval associated with the second injection phase 672. In some examples, the time interval associated with the second injection phase 672 has a duration between 30 milliseconds and 100 milliseconds and the time interval associated with the third injection phase 674 has a duration between 100 milliseconds and 1000 milliseconds.

More generally, the duration of each phase may depend on the diameter of the injectate stream, the properties of the injectate, the characteristics of the tissue at the injection site and so forth. Thus, the injection profile may usefully employ any durations suitable for accelerating to a piercing velocity sufficiently rapidly to avoid substantial loss of injectate, maintaining a piercing velocity until a target depth (e.g., subcutaneous depth) is achieved, and then maintaining a non-piercing velocity to deliver a full dose at the target depth.

It will also be understood that, while a single injection cycle is illustrated, the injection device 100 contemplated herein may usefully be configured for multiple, sequential injections. As such any number of injection cycles might usefully be performed, and any such multi-injection applications are expressly contemplated by this description.

2.1 Rotary Motor Speed

Figure 7:
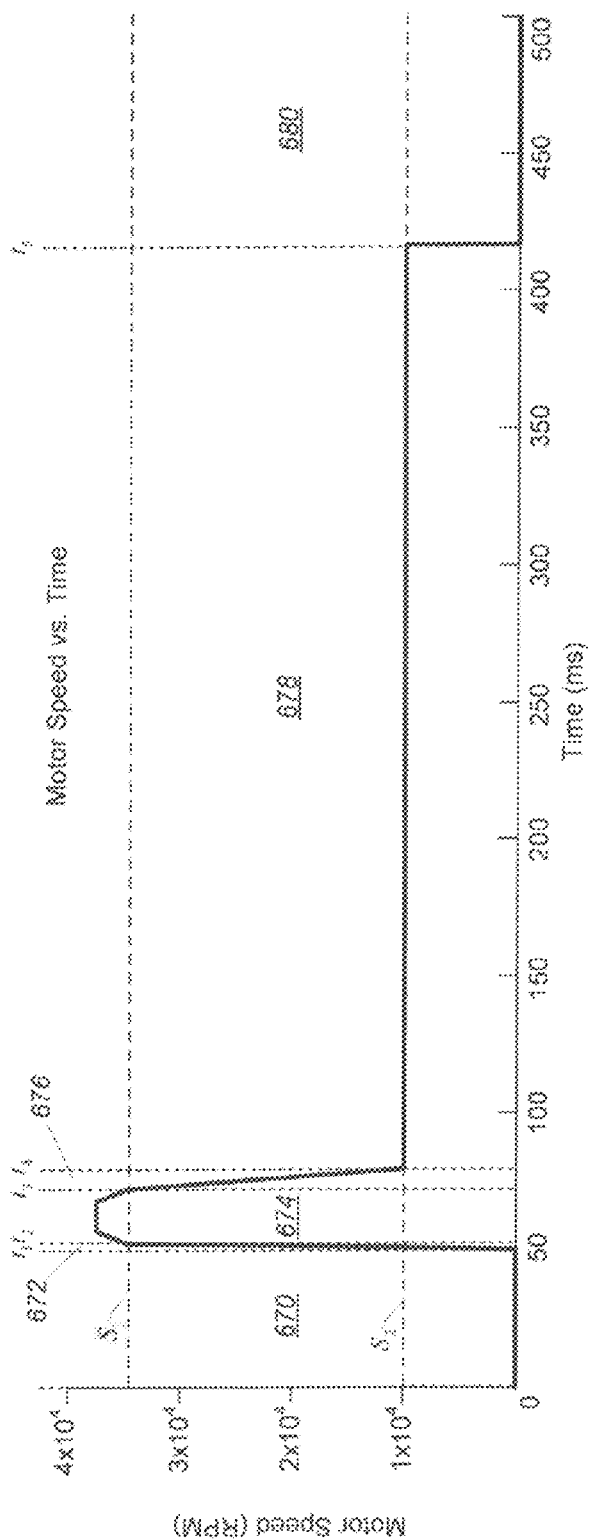
FIG. 7 is a rotary motor speed profile associated with the target displacement profile of FIG. 6.

Referring to FIG. 7, in the first injection phase 670, the injection controller 135 controls the rotary motor 126 to maintain its speed at substantially 0 rotations per minute (RPM) to ensure that the plunger 120 remains stationary at the initial position $p_0$. This may include actively maintaining the rotary motor 126 in a fixed position, e.g., by monitoring the position and activation the rotary motor 126 in counter-response to any detected motion or drift, or by control a magnetic, mechanical, or electromechanical lock that securely engages the plunger 120 in the initial position $p_0$. In another aspect, this may include passively maintaining the rotary motor 126 in the fixed position by withholding control signals or drive signals from the rotary motor 126. It will also be understood that combinations of the foregoing may advantageously be employed. For example, the plunger 120 may be locked with a mechanical lock during storage or while otherwise not in use, and then the rotary motor 126 may be used to electromechanically and actively lock the position of the plunger 120 when the mechanical lock is disengaged to prepare for an injection. In this manner, power may be conserved during long term storage, while the position can be securely and controllably locked using the rotary motor 126 in an interval immediately prior to injection in order to prevent, e.g., leakage of an injectate.

In the second injection phase 672, the injection controller 135 may control the rotary motor to accelerate from 0 RPM to a first rotary motor speed $S_1$ (e.g., 33,000 RPM), causing the plunger 120 to move from the initial position $p_0$ to the first position $p_1$. In the third injection phase 674, the injection controller 135 may control the rotary motor 126 to maintain a speed at or above the first rotary motor speed $S_1$, causing the plunger 120 to move from the first position $p_1$ to the second position $p_2$. In the fourth injection phase 676, the injection controller 135 may control the rotary motor 126 to decelerate to a second rotary motor speed $S_2$ (e.g., 11,000 RPM) less than the first rotary motor speed $S_1$, causing the plunger 120 to move from the second position $p_2$ to a third position $p_3$. In the fifth injection phase 678, the injection controller 135 may control the rotary motor 126 to maintain the second rotary motor speed $S_2$, causing the plunger 120 to move from the third position $p_3$ to a fourth position $p_4$ at a substantially consistent rate for delivery of an injectate at a target depth for an injection.

In the sixth injection phase, the injection controller 135 may control the rotary motor 126 to decelerate its speed from the second rotary motor speed $S_2$ to 0 RPM, causing movement of the plunger 120 to substantially halt at the fourth position $p_4$.

While the supercapacitor 564 in the power supply 143 described above may be used during any portion of the injection delivery, the supercapacitor 564 may be particularly advantageous where high mechanical loads are anticipated, e.g., during the initial acceleration and piercing phases, as well as where necessary or helpful to quickly decelerate or stop the plunger 120, e.g., at the fourth position $p_4$. Thus, the supercapacitor 564 may be specifically used during the second injection phase 672, the third injection phase 674, and optionally the fourth injection phase 676 if high power is required to maintain a target speed even during a deceleration of the injectate to a drug delivery velocity, and/or if high power is required to quickly decelerate or stop the plunger 120.

2.2 Injectate Velocity

Figure 8:
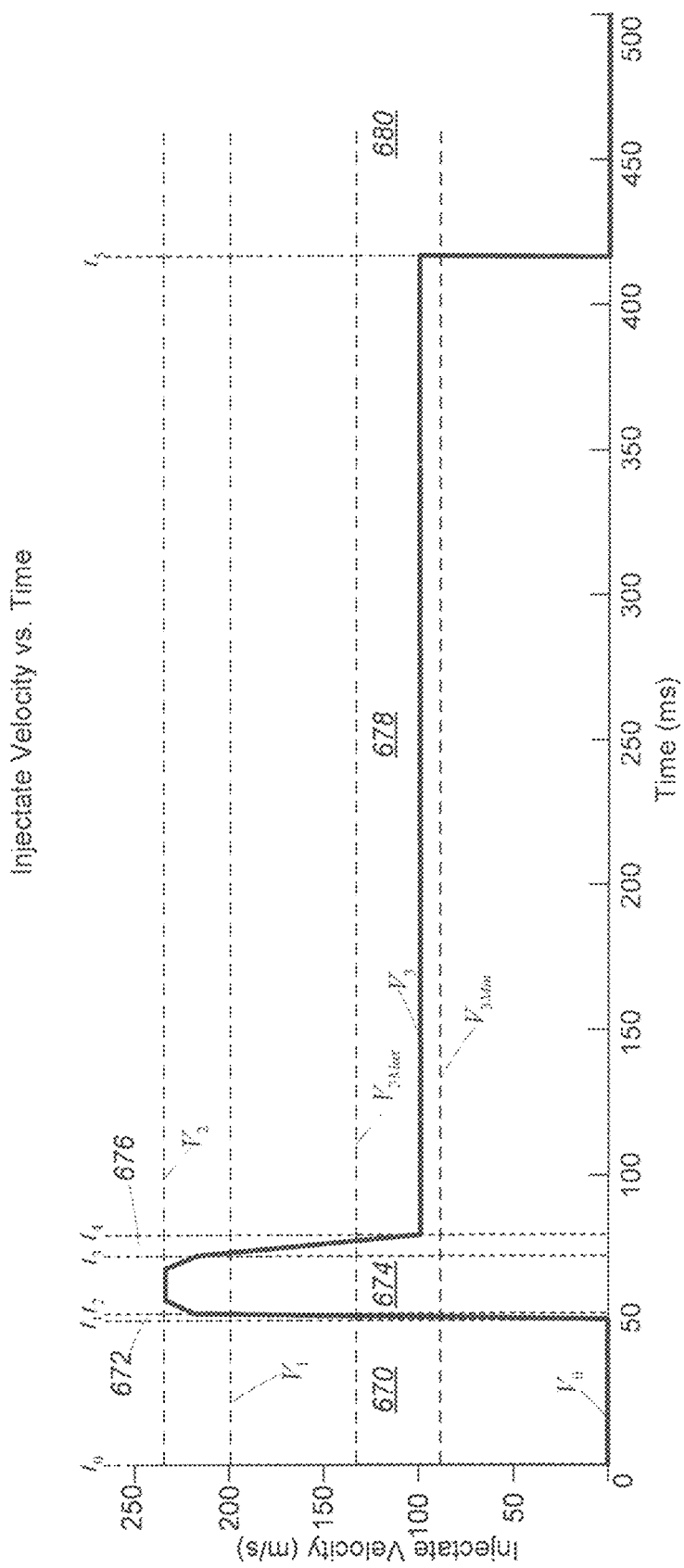
FIG. 8 is an injectate jet velocity profile associated with the target displacement profile of FIG. 6.

Referring to FIG. 8, in the first injection phase 670, no injectate is ejected from the chamber 106 (i.e., the initial injectate velocity, $V_0$ is 0 m/s). In the second injection phase 672, the injectate velocity increases from 0 m/s to the first velocity, $V_1$ at least sufficient to pierce human tissue. In some examples, the first velocity $V_1$ is at least 200 m/s. If piercing is not initiated quickly, then there may be substantial loss or leakage of drug. Thus, in some embodiments, the rotary motor 126 may usefully be configured to reach the first velocity $V_1$ for injection from a stationary starting point in not more than three rotations, such as less than two rotations, or less than one rotation.

In the third injection phase 674, the injectate velocity may be maintained at a second velocity $V_2$ greater than or equal to the first velocity $V_1$ in order to continue piercing tissue at a target site. Where the first velocity $V_1$ is a minimum velocity for piercing tissue, then the second velocity $V_2$ is preferably maintained above the first velocity $V_1$ in order to continue piercing throughout the third injection phase 674. However, the first velocity $V_1$ may instead be a minimum velocity or an optimum velocity to initiate piercing, in which case the second velocity $V_2$ may usefully be any velocity greater than, equal to, or less than the first velocity $V_1$ suitable for continuing to pierce tissue to the desired, target depth. Similarly, the second velocity $V_2$ may vary over the duration of the third injection phase 674 provided that the second velocity $V_2$ remains within this window of useful piercing velocities.

In the fourth injection phase 676, the injectate velocity may decreases to a third velocity $V_3$ (in a range between a maximum third velocity $V_{3Max}$ and a minimum third velocity $V_{3Min}$) sufficient to deliver the majority of the injectate in the chamber 106 at a subcutaneous depth. In the fifth injection phase 678, the injectate velocity may be substantially maintained at the third velocity $V_3$ while the majority of the injectate in the chamber 106 is delivered to the subcutaneous depth through the channel created during the third injection phase 674. It will be appreciated that the third velocity $V_3$ may vary over the course of the fifth injection phase 678 between any values—typically greater than zero and less than a piercing velocity—consistent with delivery of the injectate at the target depth. Finally, in the sixth injection phase 680, the injectate velocity may decrease to 0 m/s as the injection operation completes.

3 Injectate

In some examples, the volume of injectate in the chamber is at least one milliliter. Thus, in one aspect the injection device 100 may be configured to deliver one milliliter of drug subcutaneously in a single dose, or as a number of sequential doses over time, e.g., to different locations or over the course of an extended dosing schedule. Where a large number of sequential doses are intended, or where a larger single dose is intended (e.g., more than one milliliter) the chamber may usefully have a greater volume. For multi-dose applications, the contents of the chamber 106 may be conveniently distributed in discrete doses using a rotary motor and linear drive system as contemplated herein. In some examples, the volume of injectate in the chamber is less than or equal to approximately 0.5 milliliters. In some examples, the volume of injectate in the chamber is less than or equal to approximately 0.3 milliliters. In some examples, the volume of injectate in the chamber is a therapeutic amount of injectate.

In some examples, the injectate includes a biological drug. In some examples, the injectate has a viscosity of at least three centipoise at a temperature between two degrees and twenty degrees Celsius. In some examples, the injectate has a viscosity of about three centipoise to about two hundred centipoise at a temperature between two degrees and twenty degrees Celsius. Thus, the system described herein may usefully be employed with large molecule therapeutics or other drugs having relatively high viscosities.

4 Miscellaneous

In one aspect, the injection controller may be configured to cause the needle-free transdermal injection device 100 to perform a number of sequential injection operations in close temporal proximity to one another. The injection device 100 may usefully be instrumented to support this operation by sensing movement of the injection device 100 and providing tactile, visible, audible, or other feedback to aid in navigating the user through a multi-injection procedure.

In another aspect, a number of sequential injection operations may be performed without having to reverse the movement of the rotary motor (i.e., to withdraw the plunger). Thus, where additional injectate remains in the injection device 100 at the end of an injection cycle sufficient for an additional dose, the rotary motor 126 may remain stationary, and a second, complete injection cycle may be initiated from this new starting position. In this context, the rotary motor 126 may be manually locked, or electromagnetically maintained in a fixed location in order to prevent leakage or other loss of therapeutic product.

In some examples, the linkage (e.g., the ball screw linkage) is bidirectionally coupled to the rotary motor and the plunger such that bidirectional displacement of contents in the chamber is possible, e.g., by moving the plunger toward an exit nozzle to eject contents or moving the plunger away from the exit nozzle to load additional drug into the injection device 100.

In some examples, the transdermal injection device includes a sensor system for detecting when the device is properly positioned for performing an injection operation. In some examples, once the device is properly positioned, the injection controller is configured to initiate the injection operation without any observable latency. That is, the sensor system may monitor the injection device 100, determine when the injection device 100 is properly positioned and stationary, and then initiate an injection. Depending on the duration and feel of the injection, the injection may usefully be preceded by a beep, vibration, or other human-perceptible signal alerting a user that the injection is about to occur.

In some examples, one or more conventional capacitors (e.g., electrolytic capacitors) can be used instead of or in addition to the supercapacitor.

In some examples the injection controller is configured to prevent two or more injection operations within a predetermined minimum injection cycle time. Thus, for example, where a dosing regimen specifies a minimum time before injections, or where an injection is being delivered as a sequence of injections in different but adjacent locations, the injection controller may monitor activation of the injection device 100 to ensure that any rules for a corresponding injection protocol are adhered to.

In some examples, the needle-free transdermal injector head is formed as a removable cartridge for containing injectate. The removable cartridge has an opening with a predetermined shape for ejecting the injectate in a stream with a predetermined shape. In some examples, the needle-free transdermal injector includes a movable cartridge door mechanism. A user can interact with the movable cartridge door mechanism to load cartridges into the needle-free transdermal injector and to unload cartridges from the needle-free transdermal injector.

While the above description relates primarily to methods and apparatuses for the injection of therapeutics through human tissue to a subcutaneous depth, it is noted that, in some examples the methods and apparatuses described above are used for injection of therapeutics through human tissue to other shallower or deeper depths. For example, the methods and apparatuses can be used for a shallow injection of therapeutics into the dermis, or for a deeper injection though the subcutaneous layer of fat and connective tissue into a patient's musculature.

5 Training Cartridges

In one aspect, there is disclosed herein a cartridge that allows a computer-controlled, motorized auto-injector to be reconfigured (via automatic software detection) for simulating an injection. This may be a simulation for training users, or for demonstrating use of the device. A variety of techniques may be used to automatically signal the insertion of a training cartridge (a cartridge intended to initiate a training simulation) or the insertion of an injection cartridge (a cartridge containing injectate for delivery to a patient) so that an injector can responsively self-configure into an appropriate operating mode.

The device may be reconfigured by detecting features of a cartridge inserted into a chamber of the injector. In general, a training cartridge may be of the same material, feel and/or shape as a regular cartridge containing a drug. The training cartridge may also include the same tip cap as an injection cartridge so that the user can fully simulate the injection experience where the first step is to remove the cap from the cartridge before inserting the cartridge into the auto-injector.

Upon detection of a training cartridge, the operating mode of the injector may be reconfigured to performing a training simulation or the like instead of a live injection. This may include having a user interface of the device show to the user that it has entered into the simulation or training mode. Then, during the simulation, the user interface may mimic the behaviors of the injector during an injection. In addition, the motor of the injector may be driven in any suitable manner, or an additional buzzer or the like may be used, to provide a tactile simulation consistent with operation of the device during an actual injection.

Upon removing the training cartridge, the injector may return to a normal operating mode for live injectors, or a detection mode where the injector waits to detect a new cartridge inserted into the injector, and to responsively sense whether the new cartridge is a training cartridge or an injection cartridge. A variety of techniques may be used to distinguish a training cartridge from an injection cartridge, e.g., as described below.

Figure 9:
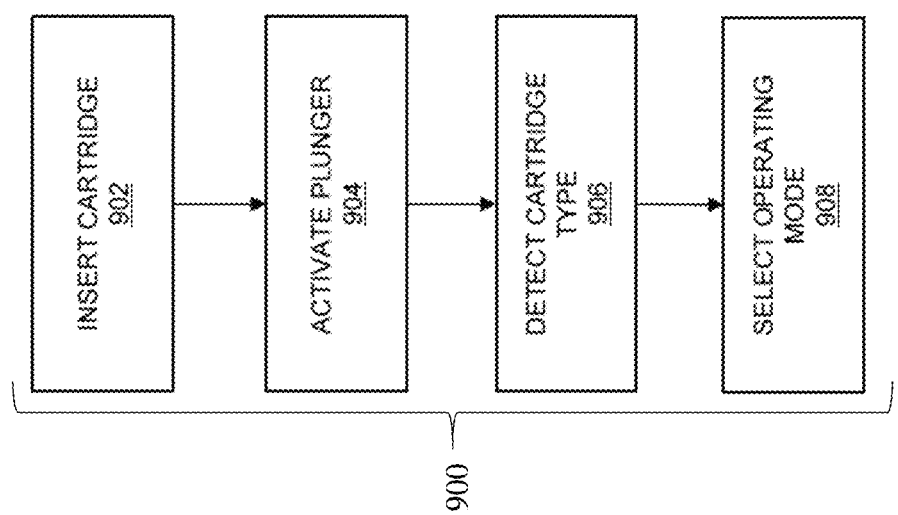
FIG. 9 shows a method for detecting a cartridge type.

FIG. 9 shows a method for detecting a cartridge type.

As shown in step 902, the method 900 may begin with inserting a cartridge such as any of the cartridges described herein into an injector such as any of the injectors described herein.

As shown in step 904, the method 900 may include activating a plunger. Using the rotary motor system described above, this may include powering the rotary motor through a motor control circuit that supplies power to the rotary motor in response to control signals from a controller. However, other linear actuators and systems may also or instead be used with the systems and methods described herein.

As shown in step 906, the method 900 may include detecting a cartridge type. In one aspect, method 900 may be used to distinguish between a training cartridge and an injection cartridge. The training cartridge will cause the injector to enter a training mode, and the injection cartridge will cause the injector to initiate an injection of cartridge contents, e.g., in a needle-free or needle-based injection as described herein. However, other types of detections may be performed. For example, the method 900 may be used to detect cartridge contents (e.g., viscosity, therapeutic type, dose volume, etc.), cartridge physical parameters (e.g., volume, orifice diameter, etc.), and so forth.

The manner of detection may also vary. For example, in one aspect the controller may detect a point at which the plunger stops moving in response to an applied linear force. Where the cartridge contains an incompressible medium or a solid, no linear motion may be possible after contact of the plunger with the cartridge contents. In response, a training cartridge may be detected. In another aspect, the point at which the plunger stops moving, e.g., the linear position where resistance is first encountered, may be used to encode cartridge information. This usefully permits multiple cartridge types to be detected, based on the linear distance traveled by the plunger before resistance is met. In another aspect, a number of flanges, rings, tabs, or the like may be fabricated on the interior wall of the cartridge, and the force required to linearly move the plunger forward through these features may vary during linear travel of the plunger. This permits more varied encoding and detection, and rather than responding to immobility of the plunger, the controller may respond to a pattern of changes in the relationship between a linear force applied by the plunger and the linear motion generated in response.

It will also be appreciated that the detection itself may use any of a variety of sensing techniques. For example, the position of the plunger may be sensed directly, or inferred based on a signal from a rotary encoder for a rotary motor used to drive the plunger. Similarly, the force applied to the plunger may be measure using any of a variety of force sensors, or may be inferred based on a measurement of the drive current supplied to the motor. The applied force may also or instead be inferred in an open loop manner based on a control signal provided by the controller to a motor controller. That is, where the power circuitry for a drive system is separate from the control circuitry of the controller, the linear force may be inferred based on calculations performed within the controller, or on a control signal output by the controller to the motor controller, based on an assumption that the drive system will produce a proportional force output. Thus, it should be understood that a sensor system, as used herein may include physical sensors such as force or distance sensors, the sensor system may also or instead include proxies for direct measurement of relevant parameters, such as a control value calculated by a controller, or a control signal that is generated as output from the controller to a motor controller or the like.

As shown in step 908, the method 900 may include selecting an operating mode. In one aspect, this may include a training mode such as any of the training modes described herein. For example, the injector may guide a user through proper placement and orientation of the injector, and provide a visual, tactile, and/or auditory signal when the injector is ready for an injection. The injector may then receive a user input and buzz or create some other injection simulation output so that the user receives feedback of a successful, simulated injection. Alternatively, where the cartridge is an injection cartridge, the injector may enter an injection mode and operate the drive system to inject a fluid from the cartridge, e.g., as described above. Where the system can detect multiple cartridge types, the controller may also configure the injector according to the cartridge type, e.g., by selecting an injection profile, injection speed, injector positioning requirements, and so forth based on the detected cartridge type.

Figure 10:
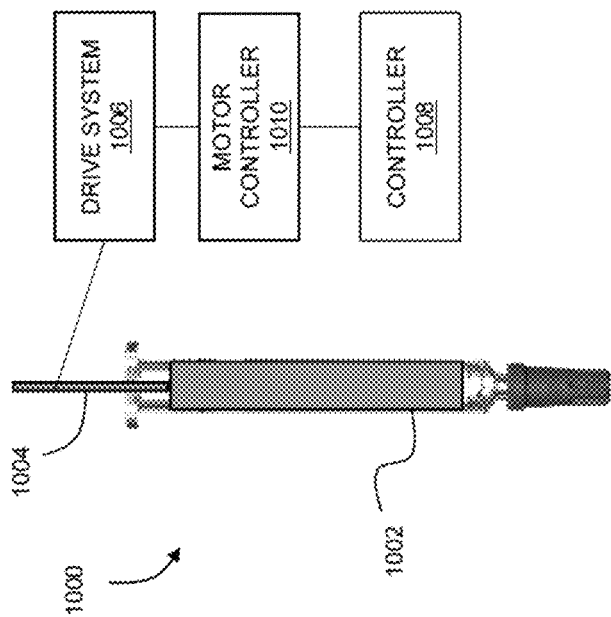
FIG. 10 shows a training cartridge detection system.

FIG. 10 shows a system using a training cartridge. The system 1000 may include a training cartridge 1002, a plunger 1004, a drive system 1006, a controller 1008, and a motor controller 1010.

In general, the plunger 1004 may be linearly actuated by the drive system 1006, in response to drive current from the motor controller 1010, which is in turn in response to a control signal from the controller 1008. In this architecture, the drive system 1006 or motor controller 1010 may include a rotary encoder or other position detection circuitry for the drive system 1006 that can be used to infer a linear position of the plunger 1004. As discussed above, it may also be possible to infer a linear force applied by the plunger 1004 to the contents of the cartridge 1002 indirectly, e.g., based on a control signal sent from the controller 1008 to the motor controller 1010, or based on a value calculated by the controller to be used as the basis for a control signal sent to the motor controller 1010.

In general, the training cartridge 1002 may be detected using any of the techniques described herein. For example, the plunger 1004 of an injector may be linearly advanced to engage a cartridge, and the controller of the injector may infer the presence of a training cartridge by the force(s) against forward movement detected by the plunger, or more generally, by the drive system.

Among the embodiments of the injector are those in which the sensor system includes a position sensor that detects the position and those in which it includes a force sensor that detects the linear force.

Also, among the embodiments are those in which the drive system includes a rotary motor. Among these are embodiments in which the position sensor includes a rotary encoder that senses rotary position of the rotary motor and embodiments in which the force sensor includes a current sensor configured to detect a drive current applied to the rotary motor.

Embodiments further include those in which the controller selects the training mode when the plunger's response to the linear force indicates that the plunger has encountered a force that varies with position of the plunger, those in which it selects the training mode when the plunger's response to the linear force indicates that the plunger has encountered a force that blocks further distal movement of the plunger, those in which it selects the training mode when the plunger's response to the linear force indicates that, at a particular location, the plunger has encountered a force that blocks further distal movement of the plunger, those in which it selects the training mode when the plunger's response to the linear force indicates that the plunger has encountered a force that resists further distal movement of the plunger, and those in which it selects the training mode when the plunger's response to the linear force indicates that the plunger has encountered a force that increases as the plunger moves distally.

In still other embodiments, the controller is configured to, after having selected the training mode, operate the plunger at a controlled rate to simulate displacement of injectate from the injection cartridge in a needle-free injection.

In some embodiments, the linear force is a first force and the change in position results from a net force that results from the first force and a second force that acts opposite to the first force to resist displacement of the plunger as the plunger is being moved distally along an axis of the cartridge. This second force, which varies with position along the axis, enables the controller to determine that the cartridge is a training cartridge.

Among the foregoing embodiments are those in which second force blocks further distal movement of the plunger beyond a particular location along the axis. Among these are embodiments in which the second force results from the plunger having encountered an incompressible medium that lies along the axis, whereby, upon encountering the incompressible medium at the particular location, the plunger is blocked from further distal movement. Embodiments include those in which the incompressible medium is a solid having a surface located at the particular location and those in which the incompressible medium is a liquid having a surface at the particular location.

In still other embodiments, the second force increases in magnitude as said plunger moves distally. Among these are embodiments in which second force results from a compressible medium against which the plunger bears during distal motion thereof.

In another aspect, the injector includes a chamber, a plunger positioned to engage a cartridge received in the chamber, a drive system that applies a force to the plunger, a sensor system configured to detect a position of the plunger, and a controller. The controller is configured to select between operating the injector in injection mode and operating the injector in training mode based on information from the sensor, the information being indicative of the plunger's response to the force.

Embodiments include those in which the controller is configured to select based at least in part on a position of the plunger, those in which the is configured to select based at least in part on a change in position of the plunger, and those in which the controller is configured to select based at least in part on rate at which the plunger is displaced, or relationship between an applied linear force and a resulting linear displacement.

In another aspect, the invention features a training cartridge for a needle-free injector. Such a training cartridge includes a body with an exterior surface shaped and sized for insertion into a chamber of the needle-free injector and a feature that causes a force that resists displacement of a plunger that is being moved distally along an axis of the training cartridge and that varies with position along the axis. Such a force enables the injector to determine that the cartridge is a training cartridge.

The above systems, devices, methods, processes, and the like may be realized in hardware, software, or any combination of these suitable for a particular application. The hardware may include a general-purpose computer and/or dedicated computing device. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. In another aspect, the methods may be embodied in systems that perform the steps thereof and may be distributed across devices in a number of ways. At the same time, processing may be distributed across devices such as the various systems described above, or all of the functionality may be integrated into a dedicated, standalone device or other hardware. In another aspect, means for performing the steps associated with the processes described above may include any of the hardware and/or software described above. All such permutations and combinations are intended to fall within the scope of the present disclosure.

Embodiments disclosed herein may include computer program products comprising computer-executable code or computer-usable code that, when executing on one or more computing devices, performs any and/or all of the steps thereof. The code may be stored in a non-transitory fashion in a computer memory, which may be a memory from which the program executes (such as random-access memory associated with a processor), or a storage device such as a disk drive, flash memory or any other optical, electromagnetic, magnetic, infrared, or other device or combination of devices. In another aspect, any of the systems and methods described above may be embodied in any suitable transmission or propagation medium carrying computer-executable code and/or any inputs or outputs from same.

The elements described and depicted herein, including in flow charts and block diagrams throughout the figures, imply logical boundaries between the elements. However, according to software or hardware engineering practices, the depicted elements and the functions thereof may be implemented on machines through computer executable media having a processor capable of executing program instructions stored thereon as a monolithic software structure, as standalone software modules, or as modules that employ external routines, code, services, and so forth, or any combination of these, and all such implementations may be within the scope of the present disclosure. Examples of such machines may include, but may not be limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices having artificial intelligence, computing devices, networking equipment, servers, routers, and the like. Furthermore, the elements depicted in the flow chart and block diagrams or any other logical component may be implemented on a machine capable of executing program instructions.

Thus, while the foregoing drawings and descriptions set forth functional aspects of the disclosed systems, no particular arrangement of software for implementing these functional aspects should be inferred from these descriptions unless explicitly stated or otherwise clear from the context. Similarly, it may be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context. Absent an explicit indication to the contrary, the disclosed steps may be modified, supplemented, omitted, and/or re-ordered without departing from the scope of this disclosure.

The method steps of the implementations described herein are intended to include any suitable method of causing such method steps to be performed, consistent with the patentability of the following claims, unless a different meaning is expressly provided or otherwise clear from the context. So, for example, performing the step of X includes any suitable method for causing another party such as a remote user, a remote processing resource (e.g., a server or cloud computer) or a machine to perform the step of X. Similarly, performing steps X, Y and Z may include any method of directing or controlling any combination of such other individuals or resources to perform steps X, Y and Z to obtain the benefit of such steps. Thus, method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity and need not be located within a particular jurisdiction.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure and are intended to form a part of the invention as defined by the following claims.

What is claimed is:

1. An injector comprising:
   a chamber that receives a cartridge,
   a plunger positioned to engage the cartridge when the cartridge has been placed in the chamber,
   a drive system coupled to the plunger for applying a linear force to drive the plunger into the chamber, wherein the drive system includes a rotary motor and a controller that controls a drive current to the rotary motor,
   a sensor system including a rotary encoder providing a signal indicative of a rotary position of the rotary motor and a drive signal indicative of a drive current supplied to the rotary motor, and
   a controller coupled to the sensor system and to the drive system, the controller comprising a memory having computer-executable code stored therein that configures the controller to select, based on information received from the sensor system, between a training mode for training a user of the injector in proper operation of the injector and an injection mode for delivering a needle-free injection from the cartridge, the information including the signal from the rotary encoder used by the controller to determine a linear position of the plunger and the drive signal used by the controller to determine a linear force applied by the drive system to the plunger, wherein the controller evaluates the manner in which the linear position of the plunger changes in response to the drive signal.

2. The injector of claim 1 wherein the drive signal is a control signal provided by the controller to a motor controller for the rotary motor.

3. An injector comprising:
   a chamber that receives a cartridge,
   a plunger positioned to engage the cartridge when the cartridge has been placed in the chamber,
   a drive system coupled to the plunger for applying a linear force to drive the plunger into the chamber,
   a sensor system configured to detect a position of a plunger and a linear force applied by the drive system to the plunger,
   a memory, and
   a controller coupled to the sensor system and to the drive system, the controller being configured by computer executable code stored in the memory to select between a training mode and an injection mode based on a change in the position of the plunger in response to the linear force.

4. The injector of claim 3, wherein the sensor system comprises a position sensor that detects the position.

5. The injector of claim 3, wherein the sensor system comprises a force sensor that detects the linear force.

6. The injector of claim 3, wherein the drive system comprises a rotary motor.

7. The injector of claim 6, wherein the position sensor comprises a rotary encoder that senses a rotary position of the rotary motor.

8. The injector of claim 6, wherein the force sensor comprises a current sensor configured to detect a drive current applied to the rotary motor.

9. The injector of claim 3, wherein the force sensor estimates the force based on a drive current supplied to the drive system.

10. The injector of claim 3, wherein the force sensor estimates the force based on a control signal sent from the controller to a motor controller for the motor.

11. The injector of claim 3, wherein the controller selects the training mode when a response of the plunger the linear force indicates that the plunger has encountered a force that varies with position of the plunger in a manner that encodes cartridge information for the controller.

12. The injector of claim 3, wherein the controller selects the training mode when a response of the plunger to the linear force indicates that the plunger has encountered a force that blocks further distal linear movement of the plunger.

13. The injector of claim 3, wherein the controller selects the training mode when a response of the plunger to the linear force indicates that, at a particular location, the plunger has encountered a force that blocks further distal movement of the plunger.

14. The injector of claim 3, wherein the controller is configured to, after having selected the training mode, operate the plunger at a controlled rate to simulate displacement of injectate from the injection cartridge in a needle-free injection.

15. The injector of claim 3, wherein the controller is configured to detect the training mode when the controller detects a substantially incompressible response of the cartridge at a predetermined linear position.

16. The injector of claim 3, wherein the injector is a needle free injector powered by a rotary motor.

17. An injector comprising:
    a chamber,
    a plunger positioned to engage a cartridge received in the chamber,
    a drive system that applies a force to the plunger,
    a sensor system configured to detect a position of the plunger, and
    a controller configured to select an operating mode for the injector based on a response of the plunger to linear actuation by the drive system.

18. The injector of claim 17, wherein the controller is configured to select the operating mode based on a change of position of the plunger.

19. The injector of claim 17, wherein the controller is configured to select the operating mode based on the change of position in response to the force applied by the plunger.

20. The injector of claim 17, wherein the operating mode includes one or more of a training mode, an injection volume mode, and an injection rate mode.

21. A training cartridge for a needle-free injector, the training cartridge comprising a body with an exterior surface shaped and sized for insertion into a chamber of the needle-free injector and a feature that causes a force that that resists displacement of a plunger that is being moved distally along an axis of the training cartridge, wherein the force varies with position along the axis, wherein the force enables the injector to determine that the cartridge is a training cartridge.

\* \* \* \* \*